United States Patent [19]

Akopov et al.

[11] 4,328,805
[45] May 11, 1982

[54] METHOD OF SUTURING THE ORGANS OF THE GASTROINTESTINAL TRACT

[76] Inventors: Ernest M. Akopov, Alexeevsky studenchesky gorodok, 6b proezd, 5a, Kv. 28; Petr M. Postolov, Sadovo-Triumfalnaya ulitsa, 4/10, kv. 105a, both of Moscow, U.S.S.R.

[21] Appl. No.: 193,887

[22] Filed: Oct. 3, 1980

[51] Int. Cl.$^3$ ............................................. A61B 17/04
[52] U.S. Cl. ........................... 128/334 R; 227/DIG. 1
[58] Field of Search .................. 128/334, 334 C, 1 R; 227/DIG. 1, DIG. 1 A

[56] References Cited

FOREIGN PATENT DOCUMENTS

516401  7/1977  U.S.S.R. ........................... 128/334 C
753430  8/1980  U.S.S.R. ........................... 128/334 R

Primary Examiner—Stephen C. Pellegrino
Attorney, Agent, or Firm—Steinberg & Raskin

[57] ABSTRACT

The present invention describes the method of suturing the stomach with the intestine, incorporating stitching up the stomach, severing the respected gastric portion, dissecting the seromuscular layers alone of the gastric wall at the place of anastomosing along the line the length of which corresponds to the required size of the anastomosis, compressing the remaining gastric portion in a close proximity to the place of the abovesaid dissection of the seromuscular layers, catching the opposite semiperimeters of the gastric wall by the mucosubmucous layers in front of the line of compression of the remaining gastric portion on the side of establishing the required anastomosis, severing the affected gastric portion some distance apart from the line of catch on the outer side of the remaining gastric portion, compressing and catching the enteric wall on its segment whose length corresponds to the size of the caught semiperimeters of the gastric wall within the zone of the anastomosis being established, followed by severing the resected enteric segment, bringing apart the caught portions of the enteric wall and the seromuscular layers of the gastric wall along the semiperimeters thereof, approximating the stomach and the intestine until the brought-apart wall portions contact each other with simultaneously apposing the semiperimeters, suturing the thus-apposed enteric and gastric walls to form a first tier of the suture that passes through all the layers of the enteric wall but only through the mucosubmucous layers of the gastric wall, releasing the walls of the organs sutured from catching and compressing, catching the seromuscular layers of the gastric wall, pulling these layers to the enteric wall and stitching them with the seromuscular layers of the enteric wall some distance apart from the first tier of the suture so that the cut of the seromuscular layers should be laid upon the first tier of the suture and the thus-formed invaginating suture be situated aside of the first tier of the suture.

5 Claims, 28 Drawing Figures

METHOD OF SUTURING THE ORGANS OF THE GASTROINTESTINAL TRACT

FIELD OF THE INVENTION

The present invention relates to methods of suturing various organs of human body and is concerned more specifically with methods of suturing the stomach with the intestine (i.e. gastroenterostomy in the case of resection of the stomach or of its walls when ablating the affected portion of the stomach without opening or exposing the cavity of the organs being sutured. The method of the present invention is applicable for establishing end-to-end, end-to-side or side-to-side anastomoses between organs differing in thickness, structure and wall properties, with an exact juxtaposition of the definite predetermined wall layers.

BACKGROUND OF THE INVENTION

Many diverse methods of suturing the stomach with the intestine are now in current use, one of which that has found extensible application in surgical practice is the method of establishing lateral gastroenteroanastomoses using the НЖКА-60 instrument, according to U.S. Pat. No. 3,079,606.

According to the above method, once the resected portion of the stomach has been removed and the remaining stump has been closed with a double-row invaginated suture, the enteric loop is passed through the opening in the transverse mesentery and fixed on the posterior wall of the gastric stump within the area of the intended anastomosis using two seromuscular stay sutures, whereupon the posterior row of seromuscular sutures is applied.

Next the posterior portion of the purse-string suture is applied (in the form of two or three stitches) to the gastric and enteric walls at the greater curvature of the stomach 10 to 15 mm away from the stay suture applied beforehand.

Then the gastric and enteric walls are pierced with a sharp-pointed scalpel on the surface somewhat away from the purse-string suture towards the lesser curvature of the stomach.

Then the jaws of the instrument stitching mechanism are introduced into the cavity of the organs being sutured through the holes pierced in the gastric and enteric walls. To provide operational convenience and prevent the gastric and enteric contents from escaping through the abovesaid holes, the intestine and the stomach must be pulled upwards by the thread of the stay suture at the greater curvature of the stomach.

Next the walls of the organs involved are compressed by the instrument jaws on the side of the mucous membrane, so that the stomach and the intestine should touch each other with their serous membranes. Thereupon the purse-string suture is completed by applying a number of stitches around the holes in the gastric and enteric walls.

After that the gastric and enteric walls juxtaposed with the serous membranes are sutured from inside by two parallel rows of stitches, whereupon the tissue between the stitches applied is severed from inside using a special change knife incorporated into the stitching mechanism of the instrument, thus establishing communication between the gastric stump and enteric loop. Next the instrument jaws are withdrawn from the cavity of the sutured organs, and the holes are stitched up by drawing the purse-string sutures, after which the purse-string sutures are invaginated by several seromuscular sutures, and the front row of seromuscular sutures is applied.

The result of gastroenterostomy established by the method described above is a put-in suture featuring the stitched up walls contacting each other with their serous membranes and diastasis of the mucous layers, with the cut of the stitched up walls situated in the cavity.

The known method of gastroenterostomy is disadvantageous in that the process of stitching the walls of the organs and severing the tissue between the sutures to establish the anastomosis is carried out from the interior of the organs being sutured, which involves opening of the cavity of these organs that hold infected contents and bringing the instrument stitching mechanism into the organs through additional holes in their walls, which must be stitched up after having withdrawn the stitching mechanism from the organs being operated. The abovesaid disadvantage leads to a considerably affected aseptic conditions of the operation, a danger of injuring the mucosa of the organs, which is sensitive to mechanical effects, with the components of the stitching mechanism, and is fraught with deformation of the organs involved due to application of additional sutures for stitching up the holes in their walls.

Another disadvantage of the above-discussed method is the fact that the cut of the walls of the organs operated upon is brought into the interior of these organs, and the surgeon cannot check whether the suture applied is hemostatic. Thus, bleeding from the anastomotic suture is oftentimes liable to occur within the postoperative period. in order to avoid this some surgeons leave part of the stomach unstitched intentionally so as to make it possible, after an anastomosis has been established, to peep at the gastric cavity through the unstitched hole so as to get sure the anastomotic suture is hemostatic.

In addition, the known method of gastroenterostomy is disadvantageous in its being applicable only in resection of the stomach by the Billroth-II technique, as it allows but side-to-side gastroenteroanastomoses to be established and fails to be applied for resection of the stomach using the most widespread and favourable Billroth-I technique involving end-to-end gastroduodenal anastomosis or the Hofmeister-Finsterer's modification of the Billroth-II technique which incorporates establishing an end-to-side gastroenterostomy.

The afore-mentioned disadvantages have by far been eliminated in one more known method of suturing the organs carried out with the use of the CK-60 instrument according to U.S. Pat. No. 3,973,709, whereby enteroanastomoses can be established by any of the now practicable techniques, viz., end-to-end, end-to-side and side-to-side.

According to the method cited above the walls of the enteric segments being sutured are compressed atraumatically, each of the semiperimeters of the wall is caught by the outer layers along the compression borderline some distance apart from the latter on the side of the resected portion of the organ, the caught semiperimeters of the walls of each compressed enteric segment are brought apart, and the organs are approximated, having apposed the semiperimeters exactly, until the brought-apart segments get in contact with each other. Then the brought-apart apposed semiperimeters are stitched up along the line of catch through all the layers of the enteric walls, the walls are released from catching and compressing, and invaginating seromuscular sutures are applied.

This method of suturing the intestines is considerably advantageous over all other heretofore known methods of suturing the organs of the alimentary tract as anastomosing is carried out without opening the cavity of the organs involved, whereby high degree of asepsis is attained. In addition, the above method enables organs to be sutured according to any of the now practicable operational techniques, whereby it would be applicable for resection of the stomach by the most commonly used Billroth-I and Billroth-II modifications involving end-to-end and end-to-side anastomoses.

However, the above-discussed method of establishing enteroanastomoses fails to be applied for suturing the stomach with the intestine, wherein the multilayer walls widely differ in the properties, interconnection and thickness, this being due the fact that suturing does not provide complete contact of the enteric gastric mucosa along the line of suture, since when the thicker wall of the stomach is caught by the outer layers only seromuscular layers of the gastric wall are brought apart and set to the suturing position, whereas the mucosubmucous layers are not involved in the suture applied. As a result, in the suture of a gastroenteric anastomosis there are stitched through all the layers of the enteric wall but the sero-muscular layers alone of the gastric walls. This is fraught with serious consequencies concerned with bleeding along the line of suture and unfavourable process of tissue regeneration. Moreover, application of a seromuscular suture invaginating its first tier and stitching the walls of the organs through all the layers, results in a very heavy torus of the anastomotic suture.

It is due to the above-mentioned disadvantages that the known advanced method of suturing the intestines cannot be applied for establishing gastroenterostomy in resection of the stomach, which is one of most frequently encountered operations. On the same account no mechanical staple suture can be applied for establishing end-to-end and end-to-side gastroenteric anastomoses in resection of the stomach by the most commonly used modifications (Billroth-I, Hofmeister-Finsterer), though such a suture allows two- or threefold reduction of the proportion of ineffective sutures applied to the organs of the alimentary tract.

SUMMARY OF THE INVENTION

It is an object of the present invention to develop a method of suturing the stomach with the intestine making it possible to ameliorate the quality of the suture applied in gastroenteroanastomoses by virtue of increased accuracy of apposition of the like layers of the walls being stitched together, also due to the provision of a reliable contact of the mucous membranes involved and attaining good hemostatic conditions of the suture, as well as by reducing the torus of the sutures applied in stitching the stomach and intestine without forming open-end exposed holes in the walls of the organs involved or opening the cavity of these organs in the course of suturing.

It is another object of the present invention to provide a possibility of resecting the stomach without opening the cavity of the organs being sutured according to the most widespread techniques, viz., Billroth-I involving an anastomosis between the end of the stitched-up stomach and the end side of the duodenum, and Billroth-II (Hofmeister-Finsterer's modification) involving an anastomosis between the end of the stitched-up stomach and the side of the small intestine.

It is one more object of the present invention to provide a possibility of resecting the stomach without opening the cavity of the organs being sutured according to the Billroth-II technique involving the establishing of side gastroenteroanastomoses.

It is still more object of the present invention to develop a method of suturing the gastric walls involving removal of the affected middle portion of the stomach and leaving the pyloric portion thereof without opening the gastric cavity, which enables the quality of the suture to be improved due to the provision of an exact apposition of the like layers of the walls being sutured, a reliable contact of the mucous membranes involved and good hemostasis, as well as a reduced torus of the sutures applied practically to the thickness of the gastric walls.

The afore-mentioned and other objects of the present invention are accomplished due to the fact that the method of suturing the stomach, with the intestine incorporates stitching up the stomach, resecting the ablated gastric portion, dissecting the seromuscular layers alone of the gastric wall at the place of anastomosing along the line whose length corresponds to the required size of the anastomosis, compressing the remaining gastric portion in a close proximity to the place of the abovesaid dissecting of the seromuscular layers, catching the opposite semiperimeters of the gastric wall by the mucosubmucous layers in front of the line of compression of the remaining gastric portion on the side of establishing the required anastomosis, severing the affected gastric portion some distance apart from the line of catch on the outer side of the remaining gastric portion, compressing and catching the enteric wall on its segment the length of which corresponds to the size of the caught semiperimeters of the gastric wall within the zone of the anastomosis being established, followed by severing the resected enteric segment, bringing apart the caught portions of the enteric wall and the seromuscular layers of the gastric wall along the semiperimeters, approximating the stomach and the intestine until the brought apart wall portions contact each other with simultaneously apposing the semiperimeters, suturing the apposed enteric and gastric walls to form a first tier on the suture passing through all the layers of the enteric wall but only through the mucosubmucous layers of the gastric wall, releasing the walls of the sutured organs from catching and compressing, catching the seromuscular layers of the gastric wall, pulling these layers to the enteric wall and stitching them with the seromuscular layers of the enteric wall some distance apart from the first tier of the suture so that the cut of the seromuscular layers should be laid upon the first tier of the suture and the thus-formed invaginating suture be situated aside of the first tier of the suture.

Such a method of suturing the stomach with the intestine provides for an adequate apposition and compression of the gastric and enteric mucous membranes in the resultant suture, as well as their reliable and tight contact, and ensures suturing of the mucosubmucous layers of the organs involved, whereby good hemostasis of the suture amenable to surgeon's supervision is obtained. The method of applying the first tier of the suture and then the second invaginating tier contributes to good apposition of the cuts of the mucosubmucous and seromuscular layers of the gastric and enteric walls and to small size of the suture torus.

Practical application of the method disclosed in the present invention makes it possible to provide better conditions for tissue regeneration, obtain more "tender" sutures of gastroenteric anastomoses and attain tissue union by first intention. It is due to this method and a positive effect of its practical application that the resection of the stomach can be carried out with the aid of suturing instrument without opening the cavity of the organs operated upon, which is of paramount importance in the case of surgery on the organs of the abdominal cavity as increasing the degree of asepsis of the operation. Besides, it becomes practically attainable to apply mechanical staple anastomotic sutures in resection of the stomach by the most commonly used and most favourable operational techniques, viz., the Billroth-I involving end-to-end anastomomosis between the stitched-up stomach and the duodenum and the Hofmeister-Finsterer's modification of the Billroth-II involving end-to-side anastomosis between the stitched-up stomach and the small intestine, as well as by some other modifications of the above-mentioned methods of resection of the stomach.

All the above-discussed enables one to reduce the occurrence of suture ineffectiveness in gastroenterostomies and attain better results of resection of the stomach.

It is desirable that the seromuscular layers of the gastric wall be caught 2 to 7 mm away from the cut formed when incising the seromuscular layers and that the enteric walls be caught 2 to 7 mm away from the first tier of the suture, as such conditions provide for a tight contact of the stitched-up gastric walls between the first and second tiers of the suture.

It is expedient in the course of suturing the intestine to the end of the stitched-up stomach and prior to cutting the seromuscular gastric walls at the place of anastomosing, to compress the angle of the stitched-up stomach along the line passing between the greater curvature of the stomach and the suture applied during its stitching, and to incise the seromuscular layers of the gastric wall along the line of the above-mentioned compression of the stomach. Such a preliminary compression of the angle of the stitched-up stomach adds to the accuracy of the required size of the anastomosis semiperimeter and to that of the arrangement of the line of the suture being applied with respect to the remaining portion of the resected stomach, and also provides for the required reliability and accuracy of the depth of incision of the seromuscular layers when resecting the stomach according to methods involving end-to-end gastroenterostomy.

It is likewise favourable in the course of suturing the intestine to the lateral gastric wall and prior to dissecting the seromuscular gastric walls at the place of anastomosing, to compress the lateral gastric wall over a length corresponding to the length of the semiperimeter of the required anastomosis, and then to cut the seromuscular layers of the gastric wall. Such a preliminary compression of the gastric side wall adds to the accuracy of the required size of the anastomosis semiperimeter and to that of the arrangement of the line of the suture being applied with respect to the remaining portion of the resected stomach and to the suture with which the gastric cavity has been stitched up, as well as provides for the required reliability and accuracy of the depth of incision of the seromuscular layers when resecting the stomach according to methods involving end-to-side anastomosis between the intestine and the stomach.

It is also advisable when suturing the gastric walls on resecting the affected middle portion of the stomach while preserving its pyloric portion, to stitch up the stomach through its sound tissues above the affected gastric portion, to incise the tissues along the applied suture between the latter and the affected gastric portion, to compress the stomach under its affected portion in the zone of sound tissues at the place of anastomosing on the side of the pyloric portion of the stomach, to dissect only the seromuscular layers of the gastric wall along the line of compression on the side of the pyloric portion of the stomach, to compress the stomach on the side of its pyloric portion in a close proximity to the place of the abovesaid dissecting of the seromuscular layers, to catch the opposite semiperimeters of the gastric wall by the mucosubmucous layers between the lines of compression beneath the affected gastric portion and on the side of the pyloric portion in a close proximity to the place of dissecting the seromuscular layers, to sever the affected portion of the stomach some distance apart from the line to catch on the outer side of the remaining pyloric portion of the stomach between the line of catch and the line of compression under the affected gastric portion, to compress the angle of the stitched-up stomach between its greater curvature and the suture with which the stomach has been stitched up, along the line whose length corresponds to the size of the caught semiperimeters of the wall at the place of anastomosing on the side of the pyloric portion of the stomach, to dissect only the seromuscular layers of the wall of the stitched-up gastric portion along the line of compression on the side of the remaining gastric portion, to compress the remaining portion of the stomach in a close proximity to the place of dissecting the seromuscular layers, to catch the opposite semiperimeters of the gastric wall by the mucosubmucous layers between the lines of compression of the angle of the stitched-up stomach and the remaining gastric portion, to sever the compressed angle of the stitched-up gastric portion some distance apart from the respective line of catch, to bring apart the caught mucosubmucous layers of the gastric wall semiperimeters on the sections facing the pyloric and stitched-up portions of the stomach to approximate the pyloric and stitched-up portions of the stomach until the opposite mucosubmucous wall layers brought apart along the semiperimeters get in comtact with each other and to simultaneously appose the contacting wall surfaces, to suture the thus-apposed mucosubmucous layers of the wall of the pyloric and stitched-up gastric portions so as to form a first tier of the suture, to release the walls of the sutured gastric portions from catching and compression, and to butt-suture the seromuscular layers of the wall of the pyloric and stitched-up gastric portions so as to form a second tier of the suture.

The method of suturing the gastric walls without opening the cavity of the remaining portions of the stomach, disclosed in the present invention is instrumental in attaining good apposition of all the gastric wall layers under high aseptic conditions and in obtaining a very small torus of the anastomotic suture, which is practically equal to the thickness of the gastric wall.

BRIEF DESCRIPTION OF THE DRAWINGS

In what follows the present invention is illustrated in a detailed description of exemplary embodiments thereof with reference to the accompanying drawings, wherein:

FIGS. 13 a, b, c, d is a schematic view of the principal stages of resection of the stomach by the Billroth-I technique;

FIGS. 14 a, b, c, d is a schematic view of the principal stages of resection of the stomach by the Hofmeister-Finsterer's modification of the Billroth-II technique;

FIGS. 18 a, b, c is a schematic view of the principal stages of resection of the stomach with the pyloric portion thereof remaining intact;

DESCRIPTION OF THE PREFERRED EMBODIMENTS

The method of suturing the stomach with the intestine set forth in the present invention, is disclosed in a specific embodiment. To effect practical implementation of the method it is expedient to use conventional stiff gastric forceps, any of the heretofore known suturing instruments, e.g., type уГ-70 according to U.S. Pat. No. 3,935,981 and type CK-60 according to U.S. Pat. No. 3,973,709. This, however, by no means excludes some other ways of practising certain individual stages of the operation, say, stitching up the stomach with a manual suture.

Once a stomach 1 (FIG. 1) has been stitched up with a suture 2 and its resected portion (not shown) has been severed, a gastric portion 4 is caught by a stiff forceps 3 at the place of anastomosing along the line whose length corresponds to the required size of anastomosis. Then seromuscular layers 5 (FIG. 2) of the gastric wall 1 are incised along the jaws of the forceps 3 on the side of the remaining gastric portion, whereby cuts 6 and 7 of the seromuscular layers 5 are brought somewhat apart. Next the portion of mucosubmucous layers 8 6 to 12 mm wide between the cuts 6 and 7 is liberated by virtue of the liability of the seromuscular layers 5 to separate rather easily from the mucosubmucous layers 8 of the gastric wall.

Then the forceps 3 (FIG. 1) is removed, and stay sutures 11 are applied to margins 9 and 10 of the gastric wall semiperimeters are held by the mucosubmucous layers 8 (FIG. 2) more closely to the distal cut 6.

Using the stay sutures 11 the stitched-up stomach 1 is put between the jaws of a respective clamp 12 of the type CK-60 suturing instrument, whereupon the walls of the stomach 1 are sutured atraumatically along the cut 7 (FIG. 2) of the seromuscular layers. Then oppositely arranged a top semiperimeter 13 (FIG. 4) and a bottom semiperimeter 14 of the compressed wall of the stomach 1 are caught by the mucosubmucous layers 8 ahead of a line 15 of compression some distance, say, 2 to 3 mm, apart therefrom on the side of establishing the required anastomosis, using fixing elements 16 of the suturing instrument CK-60 whose jaws contain also magazines 17 loaded with II-shaped staples 18, staple ejectors 19 and dies 20 with depressions for staples to bend. Once the gastric walls have been held by the mucosubmucous layers 8, the resected gastric portion 4 (FIG. 3) is severed some distance apart from a line 21 of catch outside of the remaining portion of the stomach 1.

Figure 5:
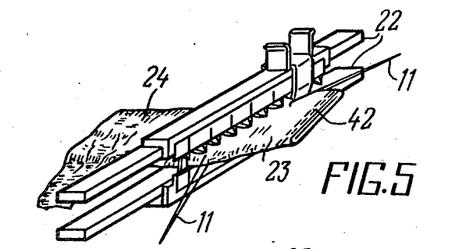
FIG. 5 is a view of the duodenum compressed between the jaws of the suturing instrument clamp at the place of anastomosing.
Figure 6:
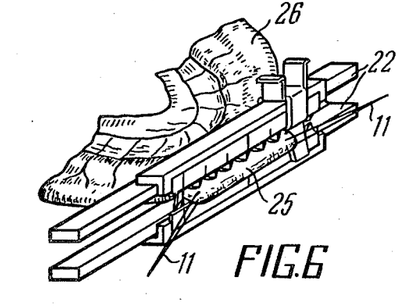
FIG. 6 is a view of the small intestine compressed between the jaws of the suturing instrument clamp at the place of anastomosing.
Figure 7:
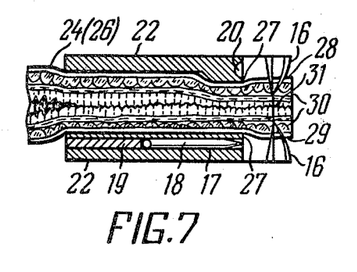
FIG. 7 is a cross-sectional view of the intestine after catching the wall semiperimeters and severing the resected gastric portion.

Using another clamp 22 (FIG. 5) of the CK-60 suturing instrument there is compressed an end 23 of a duodenum 24, or a side 25 (FIG. 6) of the duodenum or of a small intestine 26, depending upon what a modification of the stomach resection is applied. The intestinal segment 24 (FIG. 5) or 26 (FIG. 6) is so placed between the jaws of the clamp 22 that its length should correspond to the size of the caught semiperimeters of the wall of the stomach 1 (FIG. 3), and that the apposed semiperimeters of the gastric and enteric walls should not be displaced along the clamp jaws after the clamps 12 (FIG. 3) and 22 (FIGS. 5, 6) have been brought together. Thereupon a top semiperimeter 28 and a bottom semiperimeter 29 of an enteric wall 30 are caught by the fixing elements 16 2 to 3 mm apart from a borderline 27 (FIG. 7) of compression of the intestine, after which the resected enteric segment 23 (FIG. 5) or 25 (FIG. 6) is severed some distance away from a line 31 (FIG. 7) of catch.

Figure 8:
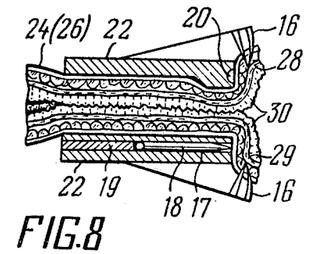
FIG. 8 is a cross-sectional view of the intestine after bringing apart the wall semiperimeters.
Figure 9:
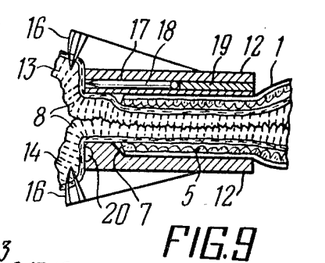
FIG. 9 is a cross-sectional view of the stomach after bringing apart the semiperimeters of the wall mucosubmucous layers.
Figure 10:
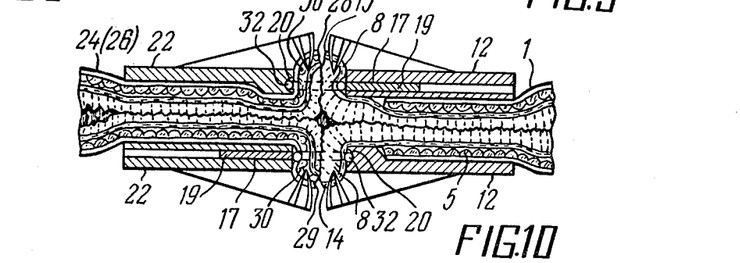
FIG. 10 is a cross-sectional view of the gastric and enteric walls after their approximating and suturing the apposed wall semiperimeters.

Then the thus-caught top semiperimeter 28 and bottom semiperimeter 29 of the enteric wall 30 (FIG. 8) and top semiperimeter 13 and bottom semiperimeter 14 of the mucosubmucous layers 8 (FIG. 9) of the gastric wall are brought apart. The organs are then approximated until the brought-apart wall portions being sutured get in contact with each other, and the semiperimeters are apposed, by bringing the instrument clamps 12 and 22 (FIG. 10) together. As a result, the mucosubmucous layers 8 of the gastric wall and all the layers of the wall 30 of the intestine 24 (26) are put between the confronted magazines 17 and dies 20 held in pairs to the top and bottom jaws of the clamps 12 and 22.

Then the brought-apart and apposed top semiperimeters 28, 13 and bottom semiperimeters 29, 14 of the enteric wall 30 are sutured through all the layers with the mucosubmucous layers 8 of the gastric wall. To this end the ejectors 19 are actuated to expel the staples 18 (FIGS. 8, 9) out of the magazines 17, whereby the legs of the staples 18 pierce the apposed top semiperimeters 28, 13 and bottom semiperimeters 29, 14 of the walls of the organs being sutured, and get bent in the depressions 20 (FIG. 10) into the B-shape or any other shape suitable for suturing to establish a staple suture 32.

Next the walls of the sutured organs are released from catching and compressing and the suturing instrument is withdrawn from the operative wound. Thus, only the mucosubmucous layers 8 of the gastric wall and all the layers of enteric wall 30 are stitched up with the staple suture 32 (FIG. 11), whereby a reliable and tight contact of a gastric mucous membrane 33 and an enteric mucous membrane 34 is attained.

Figure 11:
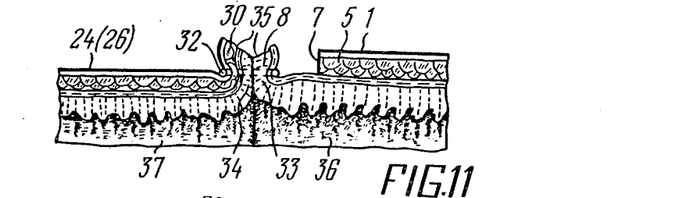
FIG. 11 is a cross-sectional view of the anastomotic suture after stitching the gastric wall through the mucosubmucous layers and the enteric wall through all its layers.

A first tier of the anastomotic suture thus applied provides for adequate apposition and compression of the gastric and enteric mucous membranes 33 and 34, respectively, as well as a reliable and tight contact thereof. In addition, stitching up of the mucosubmucous layers of the organs involved is also provided, which ensures good hemostasis of the suture under the supervision of the surgeon's eye, as the suture 35 is somewhat everted with respect to cavities 36 and 37 of the organs operated upon. The fact that only mucosubmucous layers 8 of the gastric wall are involved in the resultant suture enables one to obtain small-sized torus of the first tier 35 of the suture. In the course of application of the first tier 35 of the gastroenteroanastomotic suture, the cavity of the organs being sutured closed, whereby high degree of asepsis of the operation is provided.

Once the stomach has been stitched up with the intestine through the staple suture 32 an invaginating seromuscular suture 38 (FIG. 12) is so applied that the cut 7 of the seromuscular layers 5 of the wall of the stomach 1 should laid upon the first tier 35 of the suture. To this end the seromuscular layers 5 (FIGS. 11, 12) of the wall of the stomach 1 are caught by the suture material 2 to 7 mm away from the cut 7, pulled towards the wall 30 of the intestine 24 (26) and stitched up with seromuscular layers 39 of the enteric wall 2 to 7 mm away from the staple suture 32. The invaginating suture 38 (FIG. 12) is somewhat offset with respect to the staple suture 32 and is situated on the side of the intestine 24 (26). Highly motile seromuscular layers 5 of the wall of the stomach 1 lend themselves well to do this as if they envelop the first tier 35 of the suture.

Figure 12:
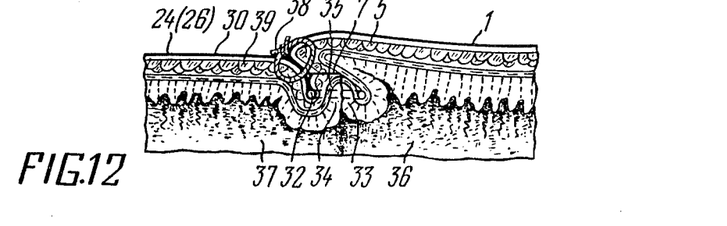
FIG. 12 is a cross-sectional view of the anastomotic suture after applying the invaginating seromuscular sutures.

The thus-applied invaginating suture 38 provides for tightness of the suture and good apposition of the seromuscular layers 5 and 39 of the walls of the stomach 1 and of the intestine 24 (26), and the mucous membranes 33 and 34 thereof. Besides, the suture 38, in combination with the first tier 35 of the staple suture, ensures small-sized torus of the suture. All this conduces to good regeneration of the stitched-up tissues and to their healing by first intention. Provision of a small-sized torus of the invaginating suture makes it possible to obtain a "delicate" elastic gastroenteroanastomotic suture without its being roughly brought into the anastomotic lumen and without constricting this lumen.

Practical application of the method of suturing the stomach with the intestine as set forth in the present invention will hereinafter be disclosed in an exemplary resection of the stomach according to the most commonly applicable and favourable operational techniques, viz., Billroth-I and Billroth-II of the Hofmeister-Finsterer's modification.

Figure 13A:
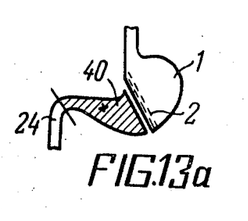
Figure 13B:
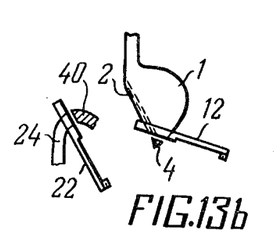
Figure 13C:
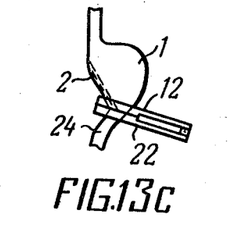
Figure 13D:
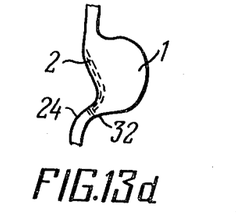

In resection of the stomach by the Billroth-I technique, an end-to-end anastomosis is established between the stitched-up stomach 1 (FIG. 13) and the duodenum 24. To this aim, after a conventional preparation of the stomach to resection, the stomach 1 (FIG. 13a) is stitched up by the suture 2 using one of the suturing instruments now in current practice, e.g., the type yΓ-70 according to U.S. Pat. 3,935,931 (the instrument being not shown in the drawing). A resected portion 40 of the stomach 1 is held by the stiff forceps (not shown) along the suturing instrument jaws and severed therealong. Then using the forceps 3 (FIG. 1) one must compress the angle 4 of the stitched-up stomach 1 along the line between the greater curvature 41 of the stomach and the suture 2 applied to the stomach to stitch it up. Then the seromuscular layers 5 (FIG. 2) alone of the gastric wall are dissected along the jaws of the forceps 3. The stitched-up portion of the stomach 1 is held by the clamp 12 (FIG. 13b) of the CK-60 suturing instrument as per U.S. Pat. No. 3,973,709, while the duodenum 24 is held by the other clamp 22 of the this instrument so that after the both clamps have been brought together, the apposed semiperimeters of the walls of the stomach 1 and the duodenum 24 should be kept against mutual displacement along the clamp jaws, whereupon the semiperimeters of the walls of the organs being sutured are caught.

The entire preparation procedure of the stomach 1 and the duodenum 24 for being held by the clamps 12 and 22 of the suturing instrument and for catching the semiperimeters of the walls of the above organs, including incision and catching of the seromuscular layers of the gastric wall at the place of anastomosing, must be carried out in keeping with the aforedescribed method of suturing the stomach with the intestine of the present invention as illustrated in FIGS. 1, 2, 3, 4, 5, and 7.

Further on, the projecting portion 4 (FIG. 13b) of the stomach 1 is severed along the jaws of the clamp 12, and the resected gastric portion 40 is devered along the jaws of the instrument clamp 22, having preliminarily compressed the portion 40 by the stiff forceps (not shown) along the jaws of the clamp 22 so as to close the lumen of the resected gastric portion 40. For the sake of convenient manipulation the end 23 (FIG. 5) of the duodenum 24 may be stitched up beforehand by a provisory staple suture 42 using any known suturing instrument, such as yΓ-70 and the resected gastric portion 40 (FIG. 13a) may be severed. Once the semiperimeters of the wall of the duodenum 24 (FIG. 7) have been caught and the end 23 (FIG. 5) thereof has been severed, the provisory suture 42 is eliminated together with the duodenal end 23.

Next the thus-fixed walls of the organs (FIGS. 8, 9) are brought apart, the clamps 12 and 22 (FIG. 13c) of the instrument are drawn together, and the apposed walls 30 (FIGS. 10, 11) of the duodenum 24 are stitched up through all the layers and the mucosubmucous layers 8 of the wall of the stomach 1. This done the thus-sutured stomach 1 (FIG. 13) and duodenum 24 are released from catching and compressing, and the suturing instrument is withdrawn from the operative wound. Then the invaginating seromuscular anastomotic sutures 38 (FIG. 12) are applied according to the method of the present invention, and the suture 2 of the stump of the stomach 1 is invaginated with seromuscular sutures (not shown) in a routine way.

Figure 14A:
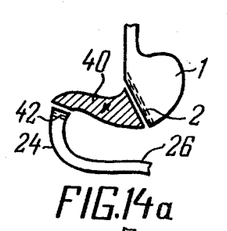
Figure 14B:
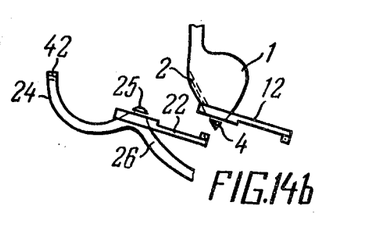
Figure 14C:
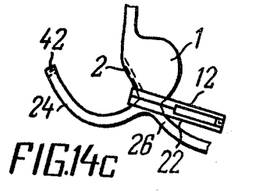
Figure 14D:
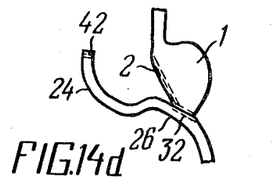

In resection of the stomach by the Hofmeister-Finsterer's modification an anastomosis is established between the end of the stitched-up stomach 1 (FIG. 14a) and the lateral surface of the small intestine 26. To this end, the stomach 1 is stitched up by the suture 2 and the duodenum 24 by the suture 42, using any known suturing instrument, say, the yΓ-70, whereupon the resected portion 41 is severed after its ends have been held by stiff forceps (not shown). Then the portion 4 (FIG. 14b) of the stitched-up stomach 1 is compressed at the place of anastomosing, by the instrument clamp 12, while the side 25 (FIGS. 6, 14b) of the small intestine 26 is compressed by the instrument clamp 22. All other stages of the operation concerned with dissecting the seromuscular layers of the wall of the stomach 1 (FIGS. 1, 2), pressing and catching the semiperimeters of the walls of the organs being sutured (FIGS. 3, 4, 6, 7, 14b), severing the resected portion 4 (FIGS. 14b, 3) of the stomach 1 and the side surface 25 (FIGS. 14b, 6) of the small intestine 26, bringing apart the apposed top semiperimeters 13, 28 (FIGS. 9, 8) and bottom semiperimeters 14, 29 of the walls of the stomach 1 and of the intestine 26, drawing together the clamos 12, 22 (FIG. 14c) of the suturing instrument, suturing the top semiperimeters 13, 28 (FIG. 10) and the bottom semiperimeters 14, 29 of the walls of the stomach 1 through the mucosubmucous layers 8 and the small intestine 26 through all its layers by the staple suture 32 (FIGS. 10, 14), applying the invaginating sutures 38 (FIG. 12) of the gastroenteroanastomosis and the invaginating suture of the gastric stump (this suture being not shown in the drawing) are in full conformity with the similar stages involved in resection of the stomach by the Billroth-I technique.

Figure 15:
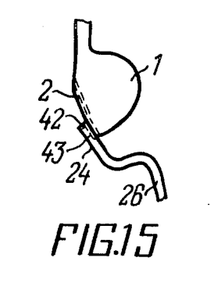
FIG. 15 is a schematic view of the organs operated upon after resection of the stomach by the Haberer-Finney's modification.

The aforestated two principal methods of resection of the stomach according to the most widespead modifications of the Billroth-I and Billroth-II techniques carried out without opening the cavity of the organs being sutured, may be considered as the basis for resection of the stomach according to some other modifications. For instance the scheme of the stomach resection by the Hofmeister-Finsterer's modification (FIG. 14) is applicable for resection of the stomach by the Haberer-Finney's modification of the Billroth-I technique, wherein a gastroenteric anastomosis 43 (FIG. 15) is established between the end of the stomach 1 stitched up by the suture 2 (FIG. 15) and the lateral surface of the duodenum 24 stitched up by the suture 42.

Figure 16:
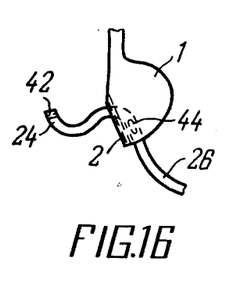
FIG. 16 is a schematic view of the organs operated upon after resection of the stomach by the Billroth-II technique.

The method of suturing the stomach with the intestine according to the present invention makes also possible application of lateral gastroenteric anastomoses 44 (FIG. 16) in, say, resection of the stomach by the Billroth-II technique.

Figure 17:
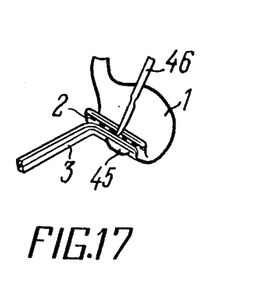
FIG. 17 is a schematic view of the stitched-up gastric stump in the course of compressing the side gastric wall.

A specific feature of the process of suturing the intestine with the lateral gastric wall consists in that, prior to dissecting the seromuscular layers of the gastric wall at the place of anastomosing a lateral wall 45 (FIG. 17) is compressed by the forceps 3 over a length corresponding to the length of the semiperimeter of the required anastomosis.

Figure 2:
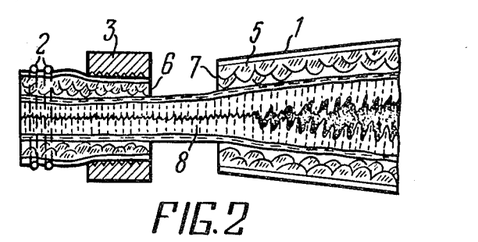
FIG. 2 is a cross-sectional view of the stitched-up stomach showing the dissected seromuscular layers.
Figure 3:
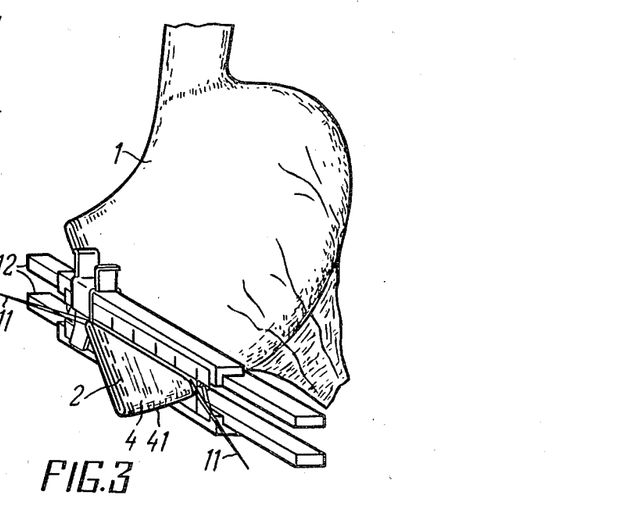
FIG. 3 is a view of the stomach compressed between the jaws of the suturing instrument clamp at the place of anastomosing.

Thereupon the seromuscular layers of the gastric wall are dissected with a scalpel 46 along the jaws of the forceps 3 in a way similar to that in preparing the end of the stitched-up stomach for suturing (FIGS. 1, 2), the forceps 3 is removed and using stay sutures passed through the mucosubmucous layers of the gastric wall in the same way as the stay sutures 11 of FIG. 3, the lateral portion of the stomach is put between the jaws of one of the instrument clamps at the place of anastomosing. All further stages concerned with compressing catching the semiperimeters of the gastric wall and with establishing a gastrointestinal anastomosis fully comply with the afore-described method of suturing the stomach of the present invention as illustrated in FIGS. 4, 6, 7, 8, 9, 10, 11, 12.

Figure 1:
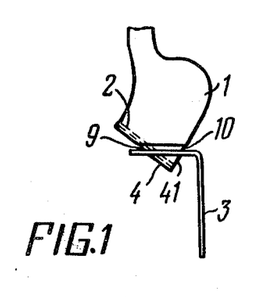
FIG. 1 is a view of the stitched-up stomach after severing the resected portion thereof.
Figure 4:
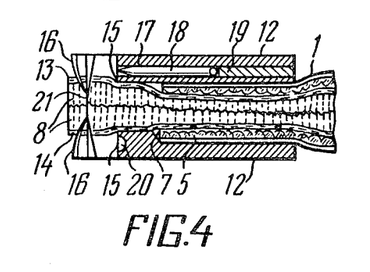
FIG. 4 is a cross-sectional view of the stomach after catching the semiperimeters of the wall mucosubmucous layers and severing the resected gastric portion.
Figure 18A:
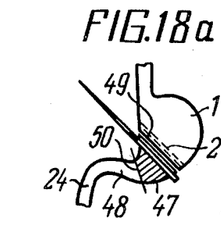
Figure 18B:
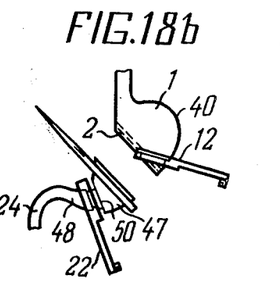

It is quite expedient for practical application to apply the method of suturing the walls of the stomach 1 (FIG. 18a) when resecting its affected portion 47 with a pyloric portion 48 of the stomach remaining intact (suprapyloric resection). The method incorporates stitching up the stomach 1 by the suture 2 in the zone of sound tissues above the affected gastric portion 47 and dissecting the tissues along a line 49 lengthwise the suture 2 between the latter and the affected portion 47. The stomach is compressed by the stiff forceps (not shown) along a line 50 beneath the affected portion 47 in the zone of sound tissues on the side of the pyloric portion 48 at the place of anastomosing. Thereupon the seromuscular layers alone of the gastric walls are dissected along the line 50 on the side of the pyloric portion 48 of the stomach as illustrated in FIG. 1. Next the pyloric portion 48 of the stomach is compressed by the clamp 22 (FIG. 18b) of the CK-60 suturing instrument in a close proximity to the place of the abovesaid dissection of the seromuscular layers, whereupon the opposite semiperimeters of the gastric wall are caught by the mucosubmucous layers 8 as shown in FIG. 4 using the instrument clamp 12, and the affected portion 47 (FIG. 18b) is severed some distance apart from the line of catch (not shown) on the outer side of the remaining pyloric portion 48 of the stomach between the line of catch and the line 50 of compression.

This terminates the preparation procedure for suturing the pyloric portion 48 of the stomach. The entire preliminary preparation for suturing the stitched-up portion of the stomach 1 fully conforms to the stages illustrated in FIGS. 1, 2, 3, 4 and considered in detail in the method of suturing the stomach with the intestine described hereinbefore. The portion 4 (FIG. 18b) of the stitched-up stomach 1 is compressed between the greater curvature 40 and the suture 2 along the line whose length corresponds to the size of the caught semiperimeters of the gastric wall at the place of anastomosing on the side of the pyloric portion 48.

Figure 18C:
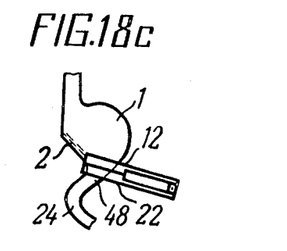
Figure 19:
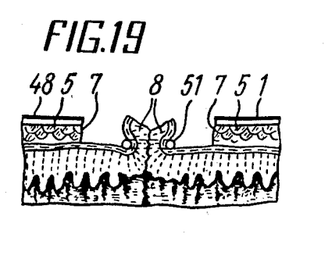
FIG. 19 is a cross-sectional view of the anastomotic suture after stitching the mucosubmucous layers of the gastric walls.
Figure 20:
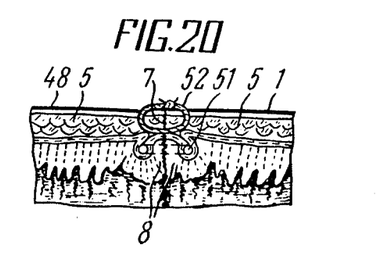
FIG. 20 is a cross-sectional view of the anastomotic suture after butt-suturing of the seromuscular layers of the gastric walls.

Further on the caught mucosubmucous layers 8 (FIG. 9) of gastric wall semiperimeters are brought apart on the segments situated on the side of the pyloric portion 48 (FIG. 18b) and of the stitched-up portion of the stomach 1, the pyloric portion 48 (FIG. 18c) is approximated with the stitched-up portion of the stomach 1 until the opposite mucosubmucous layers of the wall brought apart along the semiperimeters, contact each other, this being accompanied by apposition of the contacting wall portions, for which purpose the clamps 12 and 22 of the suturing instruments are drawn together. This done the apposed mucosubmucous layers 8 (FIG. 19) of the wall of the pyloric portion 48 and of the stitched-up portion of the stomach 1 are stitched together to form a first tier 51 of the suture, whereupon the walls of the sutured gastric portions are released from catching and compressing. When applying a second invaginating tier 52 (FIG. 20) of the anastomotic suture seromuscular layers 5 are butt-stitched manually or with the aid of a suturing instrument. The obtained suture is distinguished for good apposition of the mucosubmucous layers 8 and seromuscular layers 5 of the gastric wall and a very small torus of the anastomotic suture practically equal in thickness to the gastric wall.

Given below is a description of the surgical operation with the use of the method of the present invention.

Male patient S. (case history No. 18,806) was operated in the 1st surgical clinic of the 1st Moscow Medical Institute on Oct. 3, 1977 for cancer of the antral gastric portion using the Hofmeister-Finsterer's modification.

Superior median laparotomy was performed that detected a 4-cm tumor in the antral gastric portion, circumferentially embracing the stomach.

The stomach was mobilized along the greater and lesser curvatures. The duodenum was stitched-up by a double-row staple suture using the yΓ-70, suturing instrument. With the use of this instrument there was stitched up the stomach and severed two-third thereof. A forceps was applied to the stomach on the side of the greater curvature thereof, whereupon the seromuscular casing of the stomach was dissected along the jaws of the forceps and then shifted proximally. One of the clamps of the CK-60 instrument was applied to the thus-exposed mucosubmucous gastric membrane, while the other clamp was applied to the lateral wall of the small intestine 80 cm apart from the Treitz's ligament. Once the semiperimeters of the mucosubmucous layers of the gastric wall and all the layers of the intestinal wall had been caught, the clamps of the instrument were drawn together and a gastrojejunal anastomosis 3 cm wide was established. Then the gastric and intestinal walls were released from fixing, and the suturing instrument was withdrawn from the operative wound. Next the seromuscular casing of the stomach was stitched up with the intestine by a second tier of sutures along the line of anastomosis in such a way that the cut of the seromuscular layers of the gastric wall lay on the first tier of the suture and the stitches of the seromuscular suture was applied on the side of the small intestine.

Then the suture thus applied was check for hemostasis, and the operative wound was sutured tightly layer by layer.

The postoperative period was uneventful. The patient was dismissed from the clinic on Oct. 17, 1977.

The patient made no complaints within a 1.5-year follow-up period.

What we claim is:

1. A method of suturing the stomach with the intestine, incorporating: (a) stitching up the stomach, (b) severing the resected gastric portion, (c) dissecting the seromuscular layers along of the gastric wall at the place of anastomosing along the line whose length corresponds to the required size of the anastomosis, (d) compressing the remaining gastric portion in a close proximity to the place of the abovesaid dissecting of the seromuscular layers, (e) catching the opposite semiperimeters of the gastric wall by the mucosubmucous layers in front of the line of compression of the remaining gastric portion on the side of establishing the required anastomosis, (f) severing the affected gastric portion some distance apart from the line of catch on the outer side of the remaining gastric portion, (g) compressing and catching the enteric wall on its segment the length of which corresponds to the size of the caught semiperimeters of the gastric wall within the zone of the anastomosis being established, followed by severing the resected enteric segment, (h) bringing apart the caught portions of the enteric wall and the seromuscular layers of the gastric wall along the semiperimeters thereof, (i) approximating the stomach and the intestine until the brought-apart wall portions contact each other with simultaneously apposing the semiperimeters, (j) suturing the apposed enteric and gastric walls to form a first tier of the suture passing through all the layers of the enteric wall but only through the mucosubmucous layers of the gastric wall, (k) releasing the walls of the organs sutured from catching and compressing, (l) catching the seromuscular layers of the gastric wall, pulling these layers to the enteric wall and stitching them with the seromuscular layers of the enteric wall some distance apart from the first tier of the suture so that the cut of the seromuscular layers should be laid upon the first tier of the suture and the thus-formed invaginating suture be situated aside of the first tier of the suture.

2. A method as claimed in claim 1, wherein the seromuscular layers of the gastric wall are caught 2 to 7 mm away from the cut formed due to the above-mentioned dissecting of the seromuscular layers, while the enteric walls are caught 2 to 7 mm apart from the first tier of the suture.

3. A method as claimed in claim 1, as applied to suturing the intestine with the end of the stitched-up stomach, wherein prior to dissecting at the stage (c), the angle of the stitched-up stomach is compressed along the line between the greater curvature of the stomach and the suture applied during its stitching, whereupon the seromuscular layers of the gastric wall are dissected according to the stage (c) along the line of the abovesaid compression.

4. A method as claimed in claim 1, as applied to suturing the intestine with the lateral gastric wall, wherein prior to dissecting at the stage (c), the lateral gastric wall is compressed over a length corresponding to the length of the semiperimeters of the required anastomosis, whereupon the seromuscular layers of the gastric wall are dissected according to the stage (c).

5. A method of suturing the gastric walls when resecting the affected portion of the stomach with the pyloric portion thereof remaining intact, incorporating: (a) stitching up the stomach within the zone of sound tissues above the affected portion, (b) dissecting the tissues along the applied suture between said suture and the affected portion, (c) compressing the stomach beneath the affected portion within the zone of sound tissues on the side of the pyloric portion at the place of anactomosing, (d) dissecting the seromuscular layers alone of the gastric wall along the line of compression on the side of the pyloric portion of the stomach, (e) compressing the stomach on the side of the pyloric portion thereof in a close proximity to the place of the abovesaid dissection of the seromuscular layers, (f) catching the opposite semiperimeters of the gastric wall by the mucosubmucous layers between the lines of compression according to the compression at the stages (c) and (e), (g) severing the affected gastric portion some distance apart from the line of catch on the outer side of the remaining pyloric portion of the stomach between the line to catch and the line of compression, corresponding to the stage (c), (h) compressing the angle of the stitched-up stomach between the greater curvature thereof and the suture with which the stomach has been stitched up, along the line the length of which corresponds to the size of the caught semiperimeters of the wall at the place of anastomosing on the side of the pyloric portion of the stomach, (i) dissecting the seromuscular layers alone of the wall of the stitched-up gastric portion along the line of compression on the side of the remaining portion of the stomach, (j) compressing the remaining gastric portion in a close proximity to the place of dissection of the seromuscular layers at the stage (i), (k) catching the opposite semiperimeters of the gastric wall by the mucosubmucous layers between the lines of compression corresponding to the stages (h) and (j), (l) severing the compressed segment of the stitched-up gastric portion some distance apart from the line of catch according to the stage (k), (m) bringing apart the caught mucosubmucous layers of the semiperimeters of the gastric wall on the sections facing the pyloric and stitched-up gastric portions, (n) approximating the pyloric and stitched-up gastric portions until the opposite mucosubmucous wall layers brought apart along the semiperimeters, get in contact with each other with simultaneously apposing the contacting wall surfaces, (o) suturing the thus-apposed mucosubmucous layers of the wall of the pyloric and stitched-up gastric portions so as to form a first tier of the suture, (p) releasing the walls of the sutured gastric portions from catching and compression, (q) butt-suturing of the seromuscular layers of the wall of the pyloric and stitched-up gastric portions so as to form a second tier of the suture.

* * * * *